United States Patent
McKenzie

(10) Patent No.: US 11,896,438 B2
(45) Date of Patent: Feb. 13, 2024

(54) ORAL EXPANSION DEVICE

(71) Applicant: Charlie McKenzie, Mesa, AZ (US)

(72) Inventor: Charlie McKenzie, Mesa, AZ (US)

( * ) Notice: Subject to any disclaimer, the term of this patent is extended or adjusted under 35 U.S.C. 154(b) by 25 days.

(21) Appl. No.: 17/306,748

(22) Filed: May 3, 2021

(65) Prior Publication Data
US 2021/0338360 A1   Nov. 4, 2021

Related U.S. Application Data

(60) Provisional application No. 63/019,572, filed on May 4, 2020.

(51) Int. Cl.
*A61B 90/00* (2016.01)

(52) U.S. Cl.
CPC .................... *A61B 90/02* (2016.02)

(58) Field of Classification Search
CPC ........... A61B 90/02; A61B 17/24; A61B 1/24; A61B 1/32; A61B 1/00; A61B 17/135; A61B 2071/086; A61B 2071/088; A61M 29/02; A61M 25/1011; A61M 1/84; A61M 16/0488; A61M 16/0493; A61M 25/1002; A61C 5/90; A63B 23/03; A63B 23/032; A63B 23/18; A63B 23/185; A63B 71/085; A63B 2213/00; A61H 1/01; A61H 9/00; A61H 9/0078; A61H 13/00; A61H 2201/0103; A61H 2201/0157; A61H 2201/1253

See application file for complete search history.

(56) References Cited

U.S. PATENT DOCUMENTS

| | | | | |
|---|---|---|---|---|
| 2,493,326 | A * | 1/1950 | Trinder | A61B 17/12104 604/918 |
| 3,602,226 | A * | 8/1971 | Ericson | A61M 25/10184 604/920 |
| 5,011,474 | A * | 4/1991 | Brennan | A61M 27/00 606/196 |
| 5,362,294 | A * | 11/1994 | Seitzinger | A61B 17/0218 604/11 |
| 5,843,060 | A * | 12/1998 | Cercone | A61L 15/225 604/363 |
| 6,607,546 | B1 * | 8/2003 | Murken | A61B 17/12104 606/198 |
| 7,819,840 | B2 * | 10/2010 | Burnside | A61M 25/1029 604/910 |

(Continued)

*Primary Examiner* — Erich G Herbermann
(74) *Attorney, Agent, or Firm* — Accelerate IP

(57) ABSTRACT

An oral expansion device comprises a first body, main body and a second body wherein the first body and second body are attached to a body and a first tube and a second tube wherein the first tube and second tube having one end attached to the body and having a second end attached to an inflation device. The first tube can be attached internally to the first cavity to the inflate or deflate it and the second tube can be attached internally to the second cavity to inflate or deflate it. The body is manufactured from a flexible material. The first cavity and the second cavity can be manufactured from an inflatable material. The first cavity is an oval and the second cavity is a rectangular shape. The body has a 35-degree bend wherein the second cavity is centered on the 35-degree bend and the body can have two depressions on its sides.

7 Claims, 7 Drawing Sheets

(56) References Cited

U.S. PATENT DOCUMENTS

2005/0245906 A1* 11/2005 Makower ............ A61M 31/002
604/892.1
2013/0345628 A1* 12/2013 Berger .................. A61M 25/10
604/101.05

* cited by examiner

ORAL EXPANSION DEVICE

CROSS REFERENCE TO RELATED APPLICATION

This application claims benefit from currently U.S. Provisional Application No. 63/019,572 titled "Oral Expansion Device" and having a filing date of May 4, 2020, all of which is incorporated by reference herein.

FIELD OF THE INVENTION

The present specification relates to an oral device, more particularly an oral expansion device for stretching skin on the face of a patient.

BACKGROUND OF THE INVENTION

The utility of skin grafts is the mainstay for wound care management. When receiving a skin graft the patient's skin can become tight and uncomfortable for the patient. Therefore, there is a need for device to stretch the skin as it heals to allow for flexibility and movement. Current methods of stretching the skin involve placing the patient's or another individual's thumbs in the patient's mouth and pushing outward on the lips and cheek. This method produces an inconsistent pressure and is not uniform across all surface area in the mouth. Furthermore, prior art devices include rubber bands that are placed in the corners of the patient's mouth which provides tension that is placed on the corners of the mouth to stretch the lip from side to side. This type of device only works for the patient's lips and does not provide any pressure to the cheeks.

Therefore, there is a need for a device that provides a consistent uniform surface pressure over the cheek and lip area of the patients mouth and that allows the patient to track his/her progress during the treatment.

BRIEF SUMMARY OF THE INVENTION

In embodiment an oral expansion device for a patient having teeth and skin with an inner surface inside the patient's mount, the device comprising a main body that can be inserted into the patient's mouth between the teeth and the inner surface. A first body detachably coupled to the main body, wherein the first body has an outside surface that mechanically or through changes in pressure expands to press against the inner surface and stretch the patient's skin. The change in pressure is caused by a second body having an outer surface wherein the first body and the second body can inflate and deflate by a pump. The pump is a manual or powered pump. The first body mechanically expands by operating a knob rotatably attached to the main body wherein the knob moves a rod that is connected to an expansion member and wherein as the knob turns the rod is rotated and the expansion member moves forward and aft within the main body.

The main body can further comprise a first member contacting a second member wherein the first member tapers out towards the second member wherein the first body is connected to the main body at a pivot point. The rod can be a threaded rod. The main body can have a sliding slot wherein an expansion member is slidable within the sliding slot as the knob rotates the rod. The first body can cover the main body when in its closed position. The first body has a second slot wherein the expansion member pushes against a second slot pushing the first body outward moving the first body into its open position pushing against the patient's skin wherein the second slot is at an angle allowing the first body to raise and lower as the expansion device is moved forward and aft within the main body. The change in pressure can be caused by a first tube and a second tube which are connected to the first body and the second body wherein the first tube and second tube opposing ends are connected to the pump which inflates or deflates the first body and the second body. The main body can be manufactured from biocompatible materials that form to the patient's mouth. The first body and main body can be manufactured from material such as plastic, polyvinyl, TPU, rubber or polymer. The first body and second body can be manufactured from material such as polyvinyl, TPU, rubber or polymer.

In embodiments a method of expanding a patient's skin using an oral expansion device comprising inserting the oral expansion device into the patient's mouth. Pushing against the patient's skin by a mechanical or pressurization expansion mechanism. Monitoring the patient's progress by the turns or how much pressure is applied to the oral expansion device.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the. Absent such clear statements of intent to apply a "special" definition, it is the inventor's intent and desire that the simple, plain, and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112 (f). Thus, the use of the words "function," "means" or "step" in the Detailed Description or Description of the Drawings or claims is not intended to somehow indicate a desire to invoke the special provisions of 35 U.S.C. § 112 (f), to define the invention. To the contrary, if the provisions of 35 U.S.C. § 112 (f) are sought to be invoked to define the inventions, the claims will specifically and expressly state the exact phrases "means for" or "step for", and will also recite the word "function" (i.e., will state "means for performing the function of molding a . . . , without also reciting in such phrases any structure, material or act in support of the function. Thus, even when the claims recite a "means for performing the function of molding a . . . . , step for performing the function of molding a . . . ," if the claims also recite any structure, material or acts in support of that means or step, or that perform the recited function, then it is the clear intention of the inventors not to invoke the provisions of 35 U.S.C. § 112 (f). Moreover, even if the provisions of 35 U.S.C. § 112 (f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

Additional features and advantages of the present specification will become apparent to those skilled in the art upon consideration of the following detailed description of the illustrative embodiment exemplifying the best mode of carrying out the invention as presently perceived.

BRIEF DESCRIPTION OF THE DRAWINGS

These and other features, aspects, and advantages of the present specification will become better understood with regard to the following description, appended claims, and accompanying drawings where:

Figure 1:
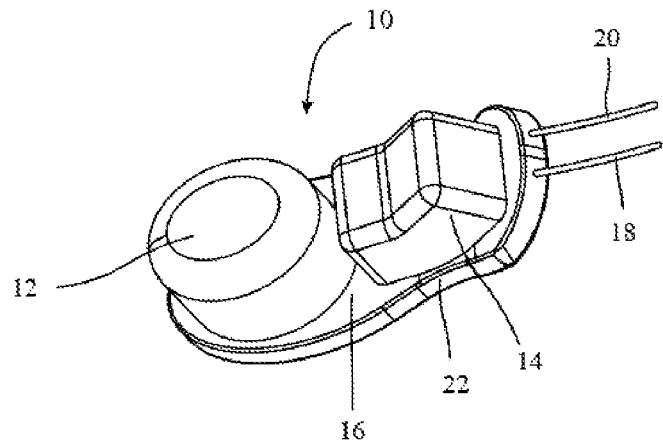
FIG. 1 is an isometric view of the oral expansion device in accordance to one, or more embodiments.
Figure 2:
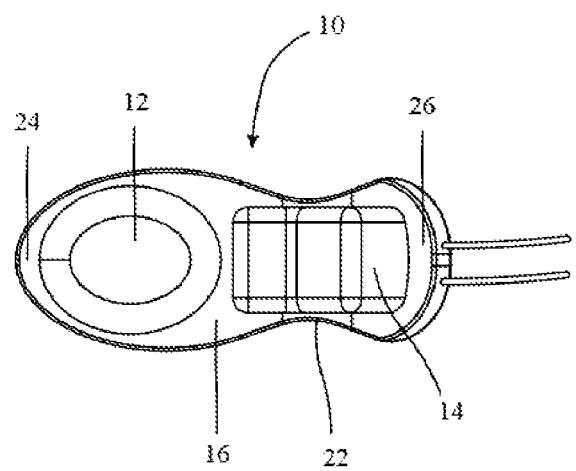
FIG. 2 is a top view of the oral expansion device in accordance to one, or more embodiments.
Figure 3:
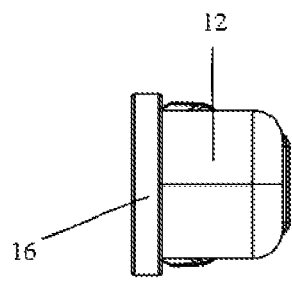
FIG. 3 is a side view of the oral expansion device in accordance to one, or more embodiments.
Figure 4:
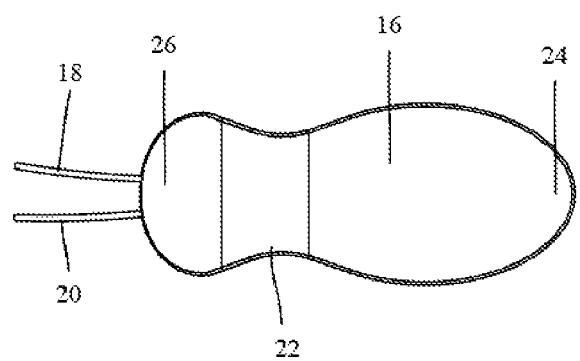
FIG. 4 is a bottom view of the oral expansion device in accordance to one, or more embodiments.
Figure 5:
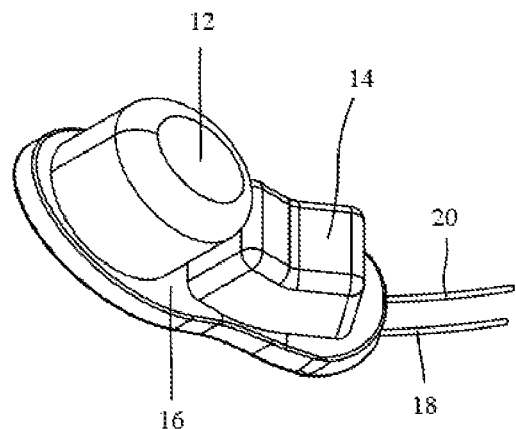
FIG. 5 is an isometric view of the oral expansion device in accordance to one, or more embodiments.
Figure 6:
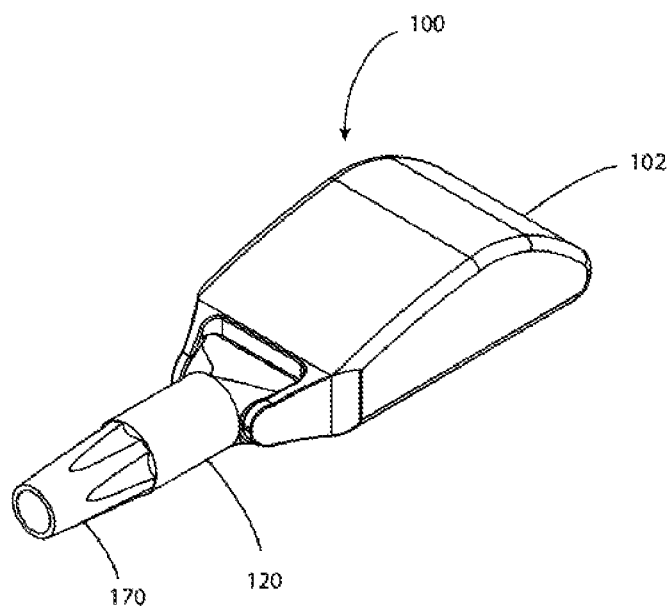
FIG. 6 is isometric view of another embodiment of the oral expansion device in accordance to one, or more embodiments.
Figure 7:
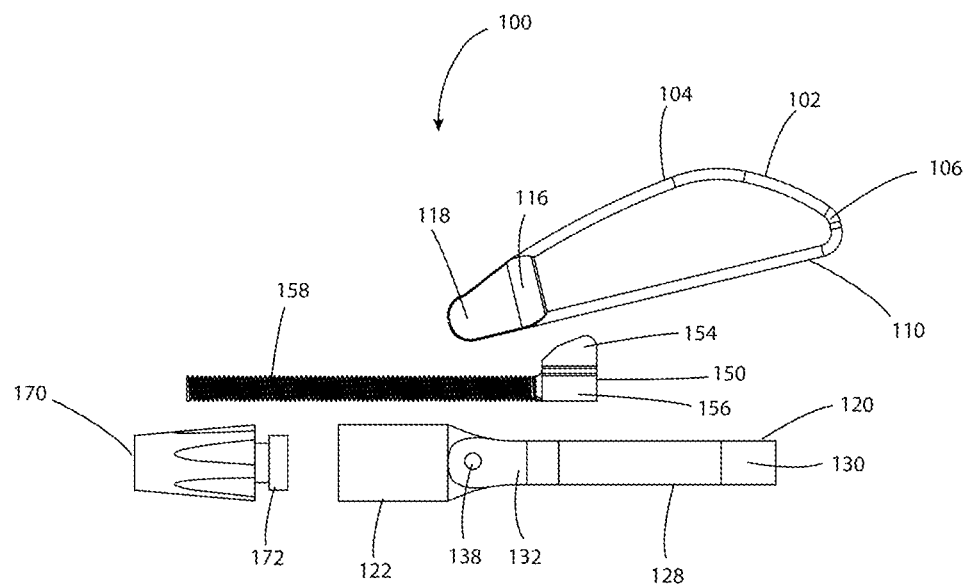
FIG. 7 is exploded side view of another embodiment of the oral expansion device in accordance to one, or more embodiments.
Figure 8:
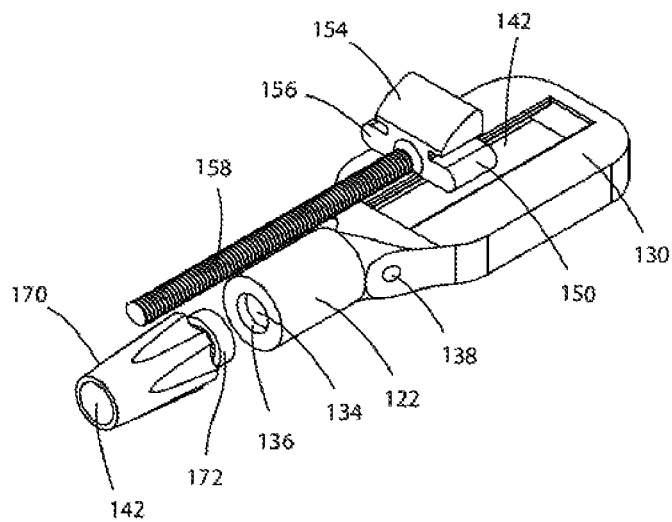
FIG. 8 is exploded isometric view omitting the first body of another embodiment of the oral expansion device in accordance to one, or more embodiments.
Figure 9:
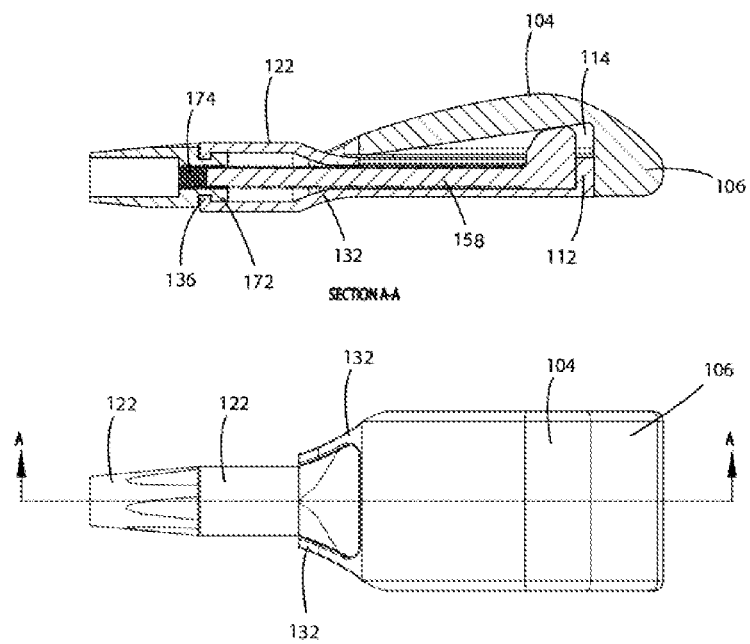
FIG. 9 is cross-sectional side view of another embodiment of the oral expansion device in accordance to one, or more embodiments.
Figure 10:
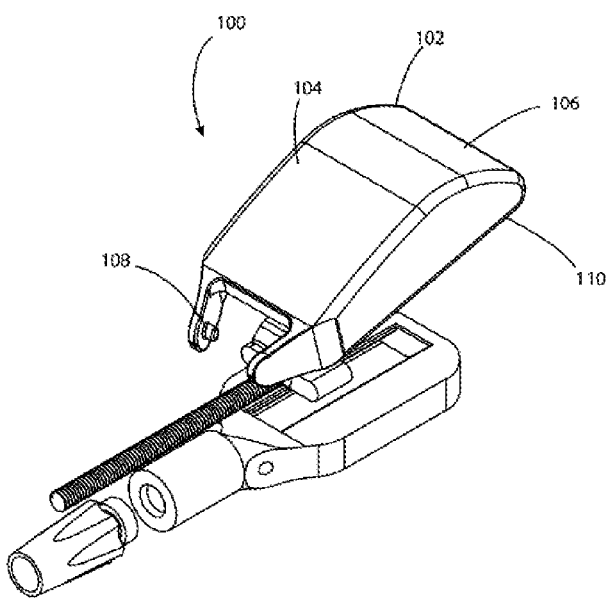
FIG. 10 is exploded isometric view of another embodiment of the oral expansion device in accordance to one, or more embodiments.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Referring initially to FIGS. 1-5, an oral expansion device for a patient having teeth and skin with an inner surface inside the patient's mouth shown generally at 10. An oral expansion device 10 can comprise a first body 12 and a second body 14 wherein the first body and second body can be attached to a main body 16 wherein the main body can be inserted into the patient's mouth between the teeth and the inner surface. The main body 16 can be manufactured from semi-rigid material and can flex when inserted into a patient's mouth. A first tube 18 and a second tube 20 can have one end attached to or integrate within the main body 16 wherein the first tube can be connected internally to the first body 12, and the second tube can be connected internally to the second body 14, the first tube and second tube's second end can be attached to a inflation/deflation device thus causing a change in pressure against the patient's cheek. The main body 12 can have a length of such as, for example, between 40 mm and 100 mm, more preferably a length of between 50 mm and 80 mm, and still more preferably a width of approximately 70 mm or the like. The main body 12 can have a width of such as, for example, between 10 mm and 70 mm, more preferably a length of between 20 mm and 50 mm, and still more preferably a width of approximately 30 mm or the like. The main body 12 can have a thickness of such as, for example, between 1 mm and 15 mm, more preferably a length of between 3 mm and 10 mm, and still more preferably a width of approximately 5 mm or the like.

The main body 12 can further comprise two depressions 22 wherein each depression can be approximate to or on the angle where the patient's mouth rests. The two depressions 22 can retain the oral expansion device 10 in the patient's mouth. The main body 12 can have a forward portion 24 and aft portion 26 wherein the forward portion and aft portion can be shaped like such as, for example, conical, parabolic, ogive, cone or the like. The aft portion 26 can accept the first tube 18 and the second tube 20 wherein the first tube and the second tube can be sealed against the aft portion creating an airtight seal. The main body 12 can further comprise a 35-degree bend at about 40 mm to 60 mm from the forward portion 24, and about 10 mm to 30 mm from the aft portion 26.

The first body 12 can be placed on the main body 12 wherein the first body's shape can be such as, for example, oval, circular, rectangular, triangular or the like, and can be placed towards the forward portion of the main body. The second body 14 can be placed on the main body 12 and centered on the 35-degree bend or can be approximate to the 35-degree bend wherein the second body's shape can be such as, for example, oval, circular, rectangular, triangular or the like. The first body 12 and second body 14 can be manufactured from material that can inflate and deflate such as, for example, polyvinylchloride, nylon, polyethylene, composite polyethylene, polyester, or the like. A pressurization expansion mechanism can expand the first body 12 and the second body 14 can be inflated or deflated by the pressurization system which can be a manual or power pump with fluid or air. The first body 12 can be placed all of the way in the patient's mouth wherein the first body can be placed against the cheek and the main body placed against the teeth. The first body 12 can expand the patient's cheek outward away from the teeth thus stretching the skin of a burn victim or an individual in need oral stretching. The first body 12 can be detachably coupled to the main body 12, wherein the first body has an outside surface that mechanically, as shown in FIG. 6-11, or through changes in pressure expands to press against the inner surface and stretch the patient's skin.

The second body 14 and/or first body 12 can be placed partially in the mouth of the patient wherein the second body and/or first body can expand outward away from the teeth when air, fluid or gas is applied to the first body and the second body stretching the cheek in an outwardly direction. The first body 12 and the second body 14 can inflate or deflate in increments which can gradually stretch the outer surface of the patient's mouth, cheeks and lips as the pressure is applied to the inside of the mouth against the cheek and lips pushing the opposite direction on the patient's teeth. The patient can track his/her progress by tracking how much air, gas or fluid is put into the first body 12 and the second body 14. In certain embodiments the first body 12 and the second body 14 can each be inflated and deflated by itself, or both can be inflated and deflated at the same time.

Referring to FIGS. 6-11, shows another embodiment including a mechanical expansion mechanism of an oral expansion device 100. The oral expansion device 100 can have a first body 102 and a main body 120 wherein the first body is detachably coupled to the main body. The first body 102 can comprise an outer surface 104 and an inner surface 110 wherein the outer surface can be shaped like an ellipse having an outer edge 106 that chamfers into a radius for easy insertion into a patient's mouth. In certain embodiments the outer surface 104 shape can be such as, for example, an egg-shape, round, eccentric, or the like. The main body 120 can have a first member 122 and a second member 130 wherein the first member can transition into the second member by a second taper 132 wherein the first member can taper or gradually increase in size out into a second member 130. The second member 130 can have a top surface 126 and a bottom surface 128 and can be substantially shaped like a rectangle with radiused corners and in other embodiments the second member can be shaped like a circle, square, hexagon, or the like. The first member 122 can be substantially circular in shape and can extend from the second member 130.

The second member 130 can have a sliding slot 124 wherein the sliding slot can be substantially centered on the second member wherein the slot can be a t-slot, or in other embodiments the slot can be a dovetail slot or the like. The sliding slot 124 can extend from one end of the second member 130 to the transition area of the second member to the first member. The first member 122 can have a thru hole 134 that can have an inner lip 136 wherein the first thru hole can extend from the front of the first member 122 to the sliding slot 124. The second taper 132 can further comprise a second thru hole 138 wherein the second thru hole can extend from one side of the second taper to the other side or in other embodiments the second thru hole can be a blind hole that does not penetrate the first thru hole 134 going through the first member 122.

Figure 11:
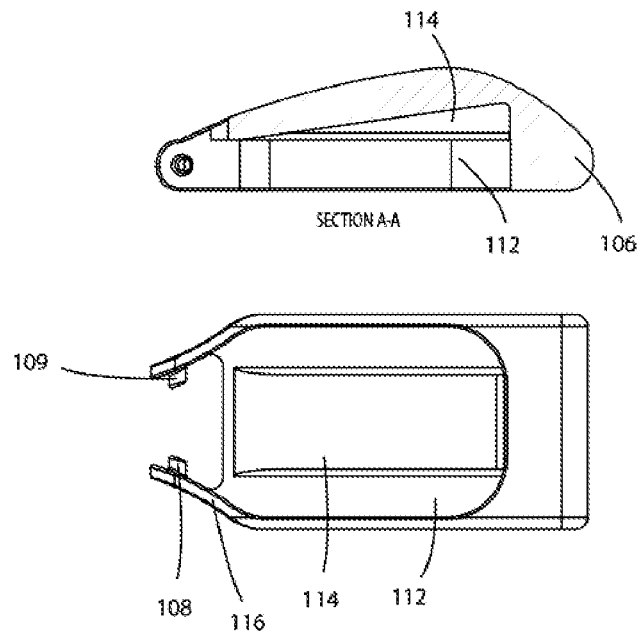
FIG. 11 is a sectional view of the first body of another embodiment of the oral expansion device in accordance to one, or more embodiments.

The first body 102 can have a first taper 116 that matches the profile of the second taper 132 wherein the first taper can extend from the first body 102 wherein the first taper can have a third slot 142 wherein the slot forms two mirrored protrusions 118 that protrude from the first body wherein the protrusions 108 have matching pins 109 on the inner side of both protrusions. The inner surface 110 can be substantially flat and can have a first slot 112 and a second slot 114 as shown in FIG. 11 wherein the first slot allows for the first body to accept and cover the sliding member 124 of main body 120. The second slot 114 can be substantially the same length as the first slot 112 wherein the second slot is at an angle wherein the angle can be such as, for example, between 1 and 45 degrees, more preferably between 5 and 25 degrees, and still more preferably approximately 10 degrees or the like.

Figure 12:
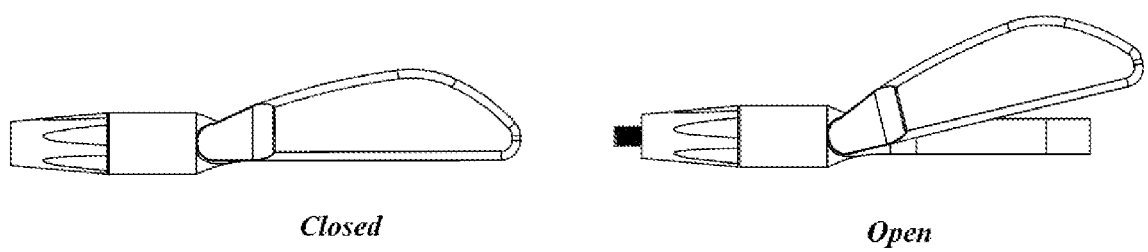
FIG. 12 is side view of another embodiment of the oral expansion device in its open and closed position in accordance to one, or more embodiments.

The oral expansion device 100 can further comprise an expansion member 150 wherein the expansion member can comprise an expansion body 152 having an upper portion 154 and a lower portion 156 wherein the lower portion is in the shape of a "T" and the upper portion has an angle can be the substantially the opposite of the second slot. Wherein the upper portion 154 can push against the second slot 114 raising the first body 102 at its pivot point away from the main body 120. The expansion member 150 can further comprise a rod 158 having threads wherein the rod extends from the lower portion. The rod 158 can be all thread, screw, bolt, threaded rod, or the like. The first slot 112 can have the substantially same shape as the second member 130 wherein when the first body is in its closed position as shown in FIG. 12 it can be substantially cover the second member. The first body 102 can be attached to the main body 120 by the protrusions 108 and the second thru hole 138 wherein the first body can pivot on the protrusions and second thru hole's axis.

Figure 13:
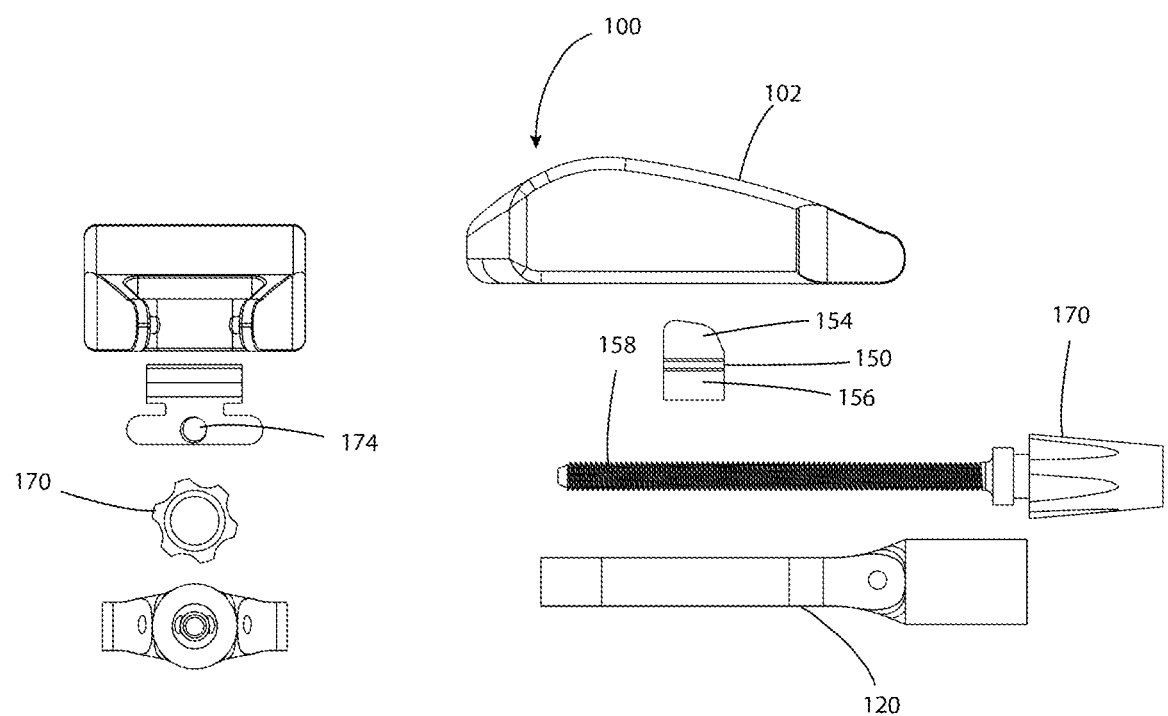
FIG. 13 is exploded front and side view of another embodiment of the oral expansion device in accordance to one, or more embodiments.

The oral expansion device 100 can further comprise a knob 170 wherein the knob can have an outer lip 172 wherein the outer lip can be contained by the inner lip 136 of the second body. The mechanical expansion mechanism can use the knob 170 which can comprise a threaded portion 174 wherein as the knob rotates about its axis the threaded portion can pull or push the rod 158 which can move forward or aft the expansion member and can either push or release the first body 102 within the third slot 142 away from the main body 120. In other embodiments, as shown in FIG. 13 the rod 158 can extend form the knob and the threaded portion can be on the expansion member 150 wherein the expansion member can slide within the third slot 142 as the knob and rod rotate.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only and is not intended to limit the scope of the present disclosure, which is defined solely by the claims. Accordingly, embodiments of the present disclosure are not limited to those precisely as shown and described.

Certain embodiments are described herein, including the best mode known to the inventors for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

What is claims is:

1. An oral expansion device for a patient having a mouth with teeth and an interior surface with skin opposite to the interior surface, the device comprising:
    a semi-rigid main body having a length, a tooth side defining a length, and a cheek side, the main body configured to be inserted into a position with the length of the tooth side abutting the teeth between the teeth and the inner surface of the patient's mouth; and
    a first body mounted on the main body opposite the tooth side such that the first body resides between the main body and the interior surface when the main body is in the position, wherein the first body has a first expanding surface that mechanically or through changes in pressure is configured to expand such that if the main body were in the position the outside surface of the first body presses against the interior surface away from the patient's teeth to stretch the patient's skin.

2. The oral expansion device according to claim 1, further comprising a second body having a second expanding surface wherein the first body and the second body can inflate and deflate by a pump.

3. The oral expansion device according to claim 2, wherein the pump is a manual or powered pump.

4. The oral expansion device according to claim 3, wherein the change in pressure is caused by a first tube and a second tube which are connected to the first body and the second body wherein the first tube and second tube opposing ends are connected to the pump which inflates or deflates the first body and the second body.

5. The oral expansion device according to claim 2, wherein the first body and second body are manufactured from material such as polyvinyl, TPU, rubber or polymer.

6. The oral expansion device according to claim 1, wherein the main body is manufactured from biocompatible materials configured to form to the patient's mouth.

7. The oral expansion device according to claim 1, wherein the first body and main body are manufactured from material such as plastic, polyvinyl, TPU, rubber or polymer.

* * * * *